United States Patent [19]
Withers

[11] Patent Number: 5,752,234
[45] Date of Patent: May 12, 1998

[54] METHOD AND APPARATUS FOR MANAGING DISPOSABLE MEDICAL SUPPLIES APPROPRIATE FOR A SINGLE PATIENT VISIT

[75] Inventor: Andrew Withers, Atlanta, Ga.

[73] Assignee: Patient Solutions, Ga.

[21] Appl. No.: 516,873

[22] Filed: Aug. 18, 1995

[51] Int. Cl.$^6$ .................................................. G06F 7/00
[52] U.S. Cl. .................................................. 705/2; 705/3
[58] Field of Search ........................... 364/401, 401 M, 364/403, 406; 395/202, 203; 705/2, 3

[56] References Cited

U.S. PATENT DOCUMENTS

| | | |
|---|---|---|
| 4,501,363 | 2/1985 | Isbey, Jr. . |
| 4,595,102 | 6/1986 | Cianci et al. . |
| 4,737,910 | 4/1988 | Kimbrow ................... 395/228 |
| 4,828,113 | 5/1989 | Friedland et al. . |
| 4,844,259 | 7/1989 | Glowczewskie, Jr. et al. . |
| 4,863,052 | 9/1989 | Lambert . |
| 4,886,165 | 12/1989 | Annett . |
| 4,890,734 | 1/1990 | Gach ........................ 206/366 |
| 4,915,233 | 4/1990 | Smith . |
| 4,954,239 | 9/1990 | Mueller . |
| 4,982,843 | 1/1991 | Jones . |
| 5,024,326 | 6/1991 | Sandel et al. . |
| 5,065,315 | 11/1991 | Garcia ..................... 395/202 |
| 5,148,920 | 9/1992 | Walker . |
| 5,148,940 | 9/1992 | Mendise ................... 220/404 |
| 5,178,417 | 1/1993 | Eshoo . |
| 5,229,584 | 7/1993 | Erickson . |
| 5,235,795 | 8/1993 | DeBusk . |
| 5,236,088 | 8/1993 | Dhority et al. . |
| 5,267,668 | 12/1993 | Jones . |
| 5,291,997 | 3/1994 | He et al. . |
| 5,310,997 | 5/1994 | Roach et al. . |
| 5,313,052 | 5/1994 | Watanabe et al. . |
| 5,323,902 | 6/1994 | Palmer et al. . |
| 5,356,006 | 10/1994 | Alpern et al. . |
| 5,356,022 | 10/1994 | Tipps . |
| 5,374,813 | 12/1994 | Shipp . |
| 5,380,994 | 1/1995 | Ray . |
| 5,401,944 | 3/1995 | Brayman . |

OTHER PUBLICATIONS

Unknown Author, In–Line Thermoforming: Key to Success of Single–Use Packaging, Package Engineeering, v25 n6, Jun. 6, 1980.

*Primary Examiner*—Emanuel T. Voeltz
*Assistant Examiner*—Phillip Groutt
*Attorney, Agent, or Firm*—Needle & Rosenberg, P.C.

[57] ABSTRACT

A method of supplying health care workers with disposable supplies appropriate for a single patient visit determines a requirement for disposable medical supplies for a patient during an associated single visit by a health care worker. An accounting code is recorded in an accounting database, the code corresponds to the disposable supplies determined to be associated with the visit. The disposable supplies are placed in a disposable container, which is delivered a first site whereat a patient is to receive treatment, prior to the visit by the health care worker. The container is subsequently delivered to a second site for disposal after the visit. Movement of the disposable container is recorded in a computer database when the disposable container is delivered to the first site and to the second site. A package for use by a health care worker in performing health care services comprises a disposable container adapted to receive disposable supplies required by the health care worker for a single visit to a patient. Means are disposed on the outside of said container for identifying the container so that it is trackable by an inventory tracking system. Means are also disposed on the outside of the container for indicating an address to which the container is to be delivered. Means are provided for sealing the container after use so that any material disposed therein cannot be accessed without breaking a seal, and for covering the address means once the container is sealed.

33 Claims, 5 Drawing Sheets

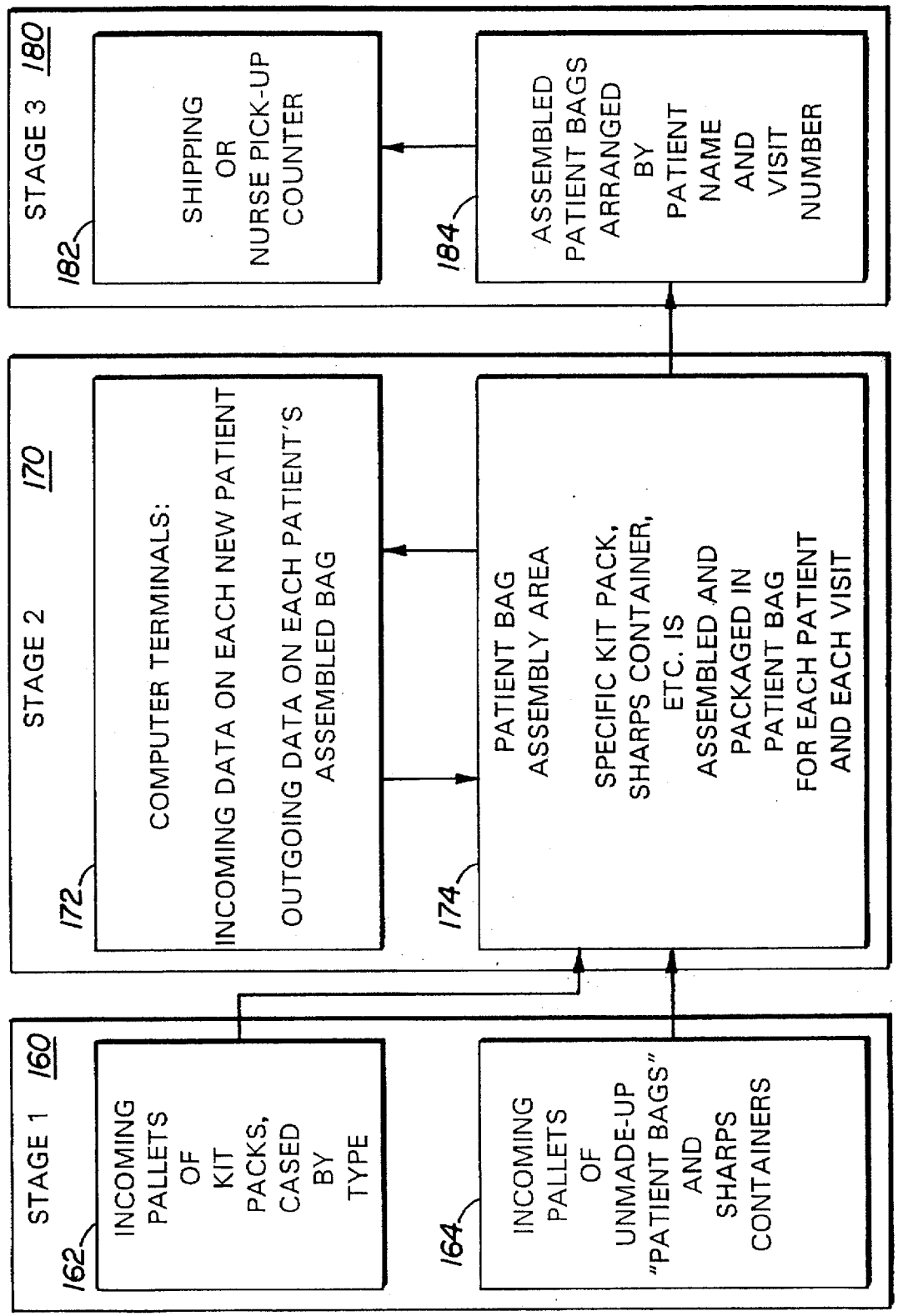

METHOD AND APPARATUS FOR MANAGING DISPOSABLE MEDICAL SUPPLIES APPROPRIATE FOR A SINGLE PATIENT VISIT

BACKGROUND OF THE INVENTION

1. Technical Field

The present invention relates to health care, and specifically to supplying health care workers with disposable supplies appropriate for a single patient visit.

2. The Prior Art

Currently, health care workers visit patients in the home, and other locations (such as nursing homes, care facilities, etc.), to perform certain health care-related tasks. Most of these workers take some kind of bag, similar to a nurses bag or a doctor's black bag, with them to carry the supplies necessary for a visit. The health care worker typically fills one bag with supplies at a central location (or takes supplies from a supply container in the trunk of her car) and takes it with her to treat several different patients. This bag will typically contain regulated disposable supplies (e.g., syringes), non-regulated disposable supplies (e.g., cotton balls) and non-disposable supplies (e.g., stethoscopes). When the visit is finished, the non-regulated disposable supplies are typically thrown in a garbage container, which is either put into the household garbage or carted back to a predetermined location for shipment to a waste disposal facility, and the regulated disposable supplies are returned to a central location for subsequent controlled disposal.

Disadvantages of this situation include the potential for contamination when one bag is shared between several patients, the risk of exposure to medical hazards by the health care worker, poor inventory control, and the potential for patients being charged for supplies not actually used in a visit.

There is little organization to the distribution of disposable supplies in situations such as home health care. Several types of medical kit packs can be found in the prior art. These are packs containing necessary supplies for a single type of home care procedure, and they generally fall into one of four categories: (1) wound treatment packs; (2) urological treatment packs; (3) intravenous packs; and (4) general care. These packs assemble supplies, but they generally provide no mechanism for disposal and tracking.

Also, there is little feedback from the off-site health care worker (off-site health care worker, as used herein, means a health care worker performing care tasks away from a hospital or other central health care location) to the system. Such feedback could be used in adjusting the treatment regime and in determining the patient's requirements for future visits. It could also be useful for analytical purposes to more efficiently allocate resources and as input for health care research.

Several distribution and tracking systems for medical supplies and medical waste are found in the prior art. Many health care providers operate under a cost reimbursement system that generally tracks general episodes of treatment rather than individual supplies used. However, nowhere in the prior art is found a system for effectively dispensing and tracking disposable medical supplies for use in health care. Also, an effective system for isolating health care patients from supplies used in visits to other patients is not found in the prior art.

Thus, it would be desirable to have a comprehensive system for assembling, maintaining, delivering, tracking and disposing of disposable supplies used in a single patient visit by a health care worker.

SUMMARY OF THE INVENTION

In one aspect, the present invention is a method of supplying health care workers with disposable supplies appropriate for a single patient visit. A requirement for disposable medical supplies is determined for a patient for an associated health care worker single visit. An accounting code is recorded in an accounting database, the code corresponding to the disposable supplies determined to be associated with the visit. The disposable supplies determined to be associated with the visit are placed in a disposable container. The disposable container and the disposable supplies are delivered to a first site, whereat a patient is to receive treatment, prior to or simultaneously with the associated single visit by the health care worker. The disposable container is delivered to a second site for disposal after the visit by the health care worker. Movement of the disposable container is recorded in a computer database when the disposable container is delivered to the first site and to the second site.

In another aspect, the present invention is a method of managing supplies required by a health care worker during a single patient visit at a first predetermined site. The procedures to be performed by the health worker during the single patient visit are determined. A database relating disposable supplies necessary in a specific procedure is accessed. The disposable supplies necessary for that procedure are placed in a disposable container. The disposable container is delivered to the first predetermined site prior to the single patient visit.

In yet another aspect, the present invention is a package for use by a health care worker in providing health care services to a patient. The package comprises a disposable container having an outside surface and defining an inside portion adapted to receive disposable supplies required by the health care worker for a single visit to a single patient. A means, such as a bar code, is disposed on the outside of the container for identifying the container so that it is trackable by a tracking system. A means, such as a label, is disposed on the outside of the container for indicating an address to which the container is to be delivered. A means, such as tape, is also provided for sealing the container after use so that any material disposed therein cannot be accessed without breaking a seal.

An advantage of the present invention is that it improves inventory management of supplies used in health care visits.

A further advantage of the present invention is that it isolates infectious materials encountered by health care workers, patients and waste disposal personnel.

A further advantage of the present invention is that it prevents a single sharps container from being used at several different treatment sites for several patients.

A further advantage of the present invention is that it allows tracking of medical waste generated by health care.

A further advantage of the present invention is that it provides secure disposal of medical waste.

These and other advantages of the present invention will be disclosed fully in the detailed description that follows.

BRIEF DESCRIPTION OF THE FIGURES OF THE DRAWINGS

FIG. 3 is a is a flow chart detailing the steps employed in a method in accordance with a second embodiment of the present invention.

DETAILED DESCRIPTION

Figure 1:
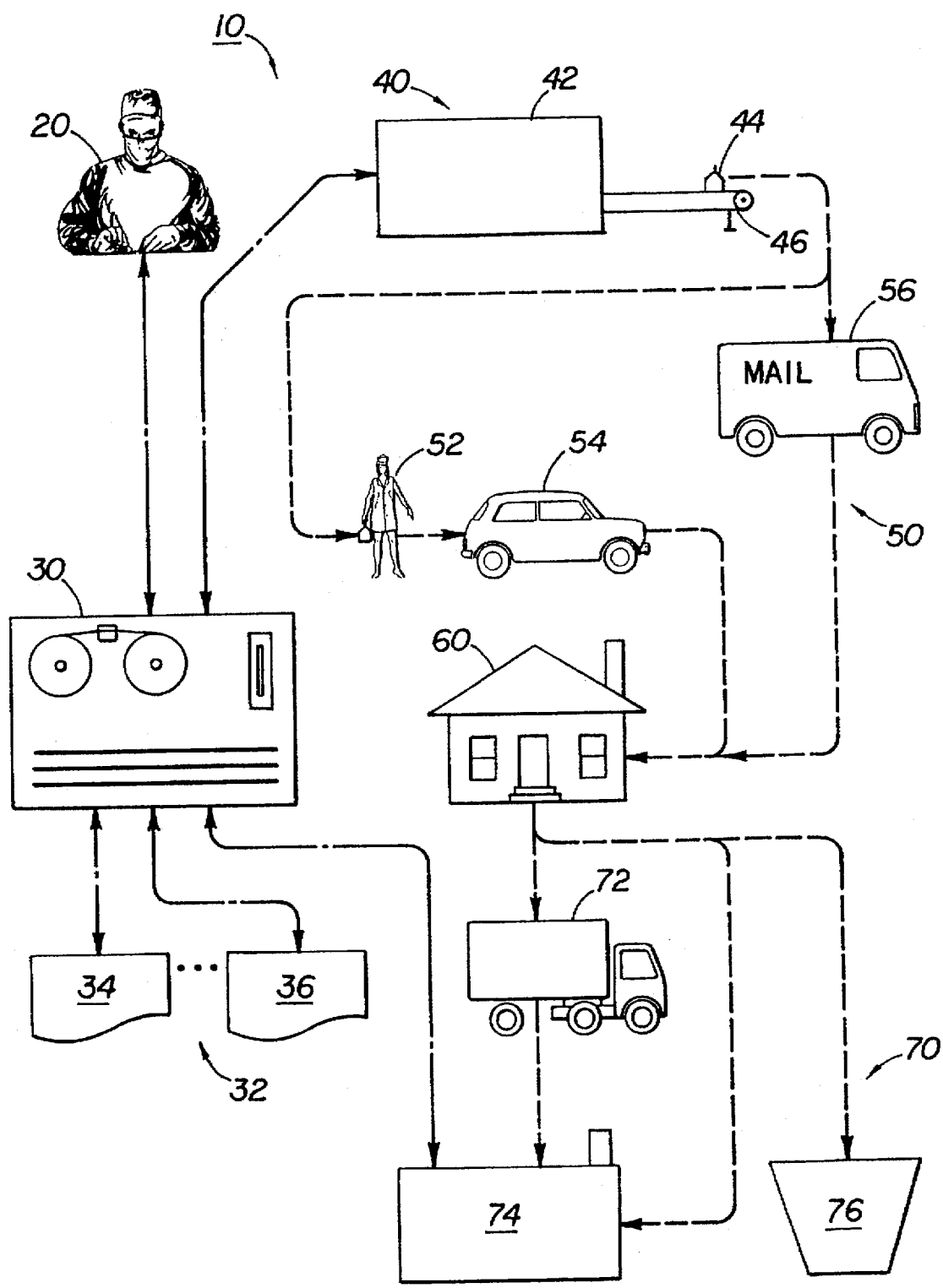
FIG. 1 is a schematic diagram showing the steps employed in a method generally in accordance with the present invention.

The invention is now described in detail. Referring to the drawings, like numbers indicate like parts throughout the views.

As used in the description herein and throughout the claims that follow, "a," "an," and "the" includes plural reference unless the context clearly dictates otherwise.

The present invention is directed to a system for supplying health care workers (such as those who provide care in the patient's home or other locations) with disposable supplies necessary for a single patient visit, separate from non-disposable supplies. It will find its primary application in situations where a patient will receive several periodic visits from a health care worker (e.g., a nurse). As generally depicted in FIG. 1, the method of the present invention 10 begins with a medical professional 20 (e.g., a physician or a physical therapist) prescribing a course of treatment for a patient to be performed at a first site, such as in the patient's home 60 or a health care facility, by a health care worker 52. Instructions for the course of treatment are transmitted to a central computer 30. The computer 30 accesses a plurality of databases 32, which include a first database 34 that relates the course of treatment to a requirement for disposable medical supplies. A second database 36 is an accounting database that maintains patient billing information and is used to post charges and accounting codes to the patient's account when supplies are prepared for a patient visit. From information contained in the first database 34, the computer 30 generates a list of supplies required for each patient visit and transmits the list to a patient visit supply processing organization 40. Other information may also be transmitted by the computer 30, including: a list of procedures to be performed, a record of the patient's medical history, directions to the patient's home, etc.

The patient visit supply processing organization 40 comprises a visit supply kit assembly facility 42, where the supplies on the list generated by the computer 30 are assembled into a visit supply package 44. Although FIG. 1 shows the computer 30 as being separate from both the health care professional's 20 office and the supply processing organization 40, it would be obvious to one skilled in the art that the computer 30 could be part of the data processing equipment belonging to the health care professional's 20 office, the care providing organization (e.g., a home nursing care company) or the supply processing organization 40.

Once the visit supply package 44 has been assembled, it is made available to a delivery system 50. The delivery system 50 could comprise the health care worker 52 physically picking up the visit supply package 44 at a depot 46 and taking it to the patient's home 60 via her automobile 54, or other form of transportation, or the visit supply package 44 may be delivered to the patient's home 60 by the mail system 56, or other similar system, prior to, or simultaneously with, the visit by the health care worker 52.

The health care worker 52 may provide feedback to the computer 30 with information such as an accounting of the actual supplies used in each procedure performed. Such information could be useful in optimizing the supplies incorporated in future visit supply packages 44. Other information could include information about the patient's condition that could be included in the patient's medical record and that could also effect the supplies required for the next visit. It is not always necessary to get feedback after any given visit, but feedback could effect supplies required for future visits.

After the visit is complete, the health care worker 52 can seal the supply package 44, containing the used disposable supplies, and dispose of it at a second site via a disposal system 70. The disposal system 70 could comprise: depositing the supply package 44 with a delivery service 72 for delivery to a waste disposal facility 74, such as a medical incinerator; the health care worker 52 delivering the supply package 44 directly to the disposal facility 74; or merely throwing the supply package 44 in a conventional garbage disposal site 76, if the situation would permit such disposal. The supply package 44 could also be returned to the health care worker's 52 original place of business for subsequent disposal. The disposal system 70 could then supply tracking information to the computer 30 providing a record of the disposal of the supply package 44.

Figure 2A:
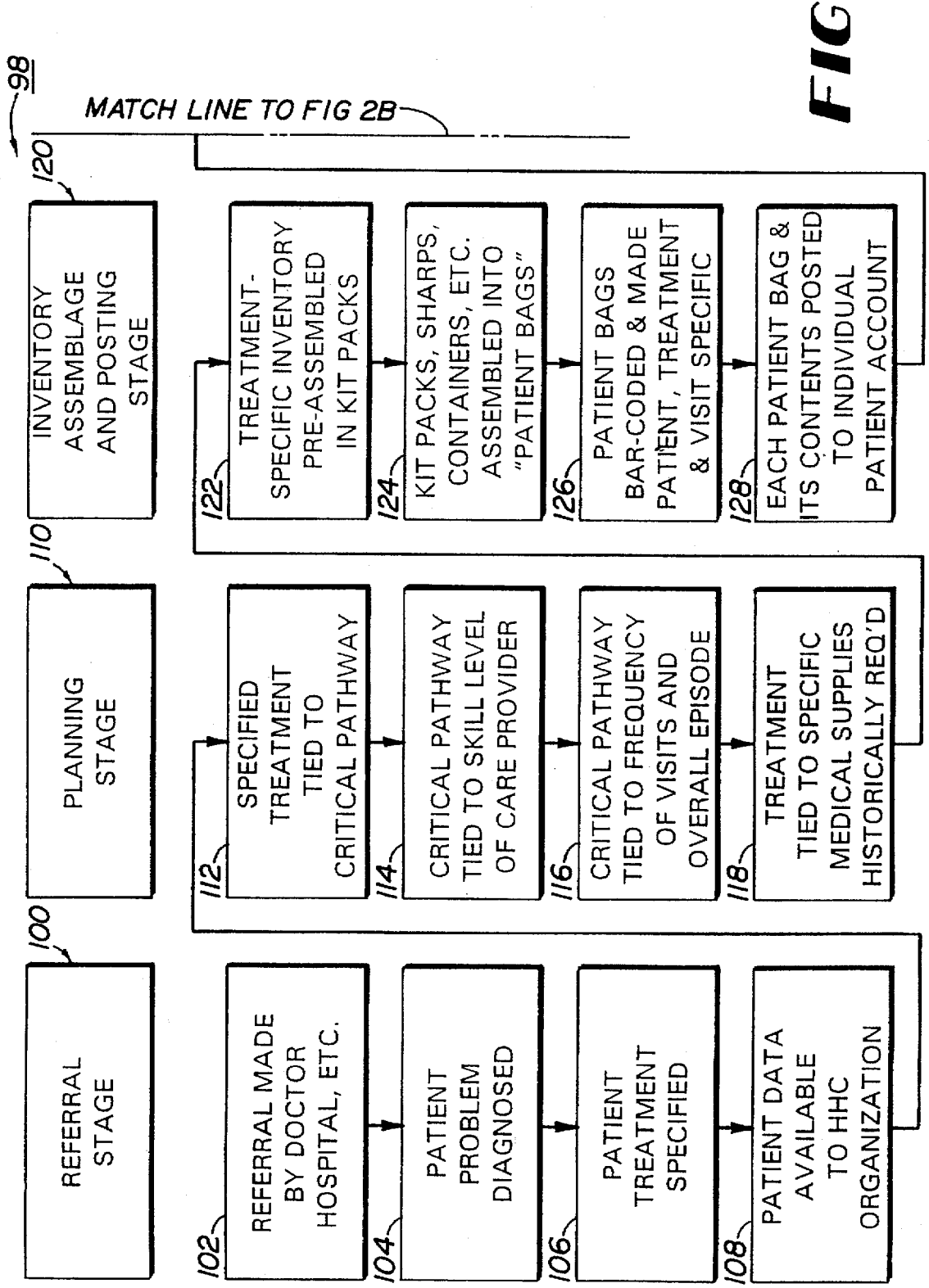
FIG. 2 is a flow chart detailing the steps employed in a method in accordance with a first embodiment of the present invention.
Figure 2B:
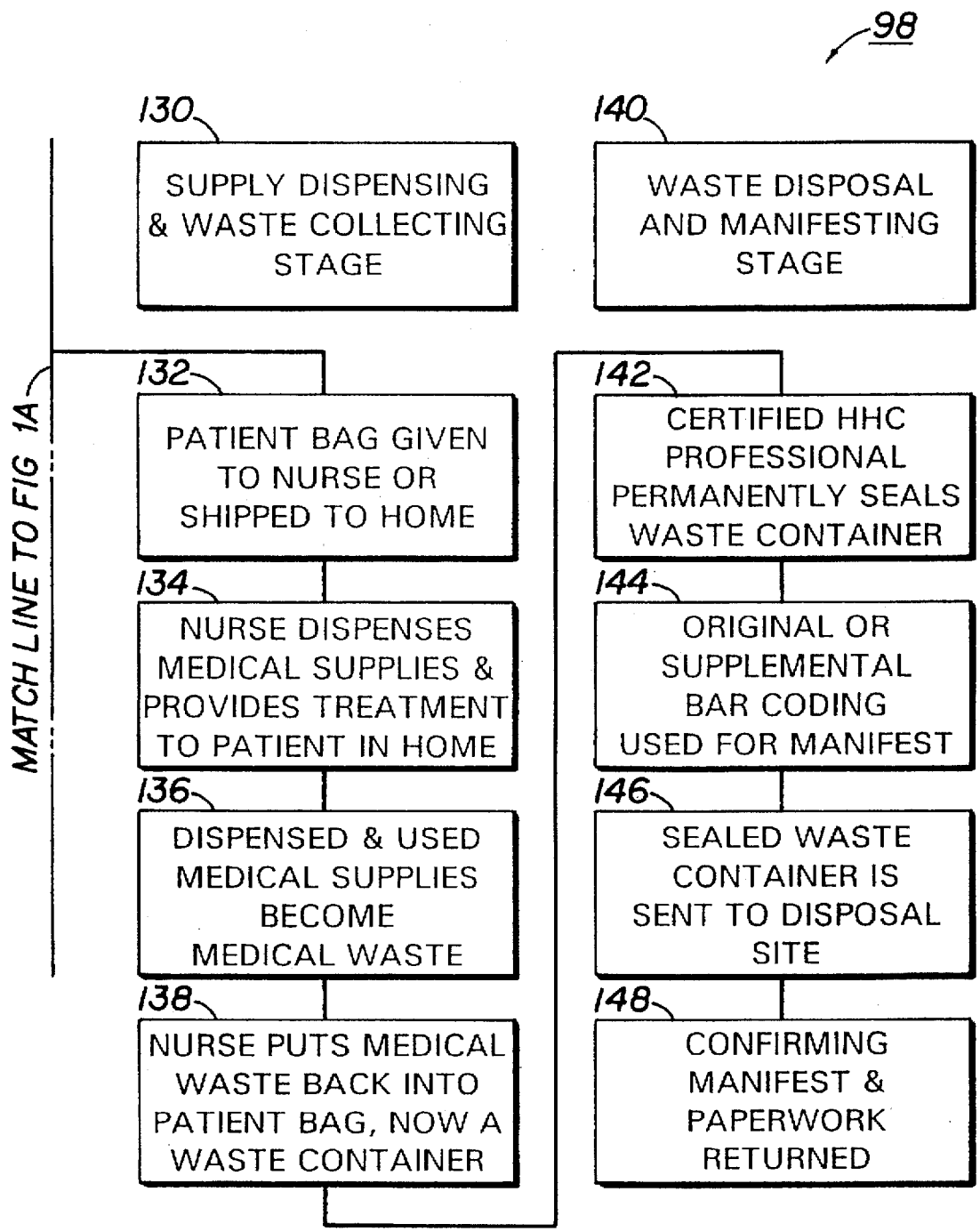

A more detailed description of the process 98 of one embodiment of the present invention is depicted in FIG. 2. One embodiment of the entire process 98 comprises five stages: a referral stage 100, a planning stage 110, an inventory assemblage and posting stage 120, a supply dispensing and waste collecting stage 130 and a waste disposal and manifesting stage 140.

In the referral stage 100, the patient receives a referral 102 to a doctor, or other health care professional or facility. The patient's problem is diagnosed 104 by the professional and a course of treatment 106 is specified, or prescribed, by the professional. At this stage data, including the course of treatment and the patient's medical history, is made available 108 to a health care organization.

In the planning stage 110, the specified treatment is tied to a critical pathway 112, which is the treatment pathway needed to most efficiently effectuate a desired outcome for a given patient. The critical pathway 112 is then tied to the skill level of a health care provider 114 and to the frequency of visits and the overall episode 116, which is the collection of treatments applied to a patient to achieve a desired result. The treatment is tied to the specific medical supplies 118 historically required by similar patients with similar treatment requirements.

In the inventory assemblage and posting stage 120, a treatment-specific and patient-specific inventory of disposable supplies is pre-assembled into kit packs 122 at the supply kit assembly facility 42. The kit packs, sharps containers, etc., are assembled 124 into patient bags, or supply packages 44. The supply packages 44 are bar-coded 126 with tracking and accounting information and are made patient, treatment, and visit specific with information regarding the visit for which the supply package 44 is being assembled. Then a list of the contents of the supply package 44 is posted 128 to the individual patient's account.

In the supply dispensing and waste collecting stage 130, the supply package 44 is given 132 either directly to the health care worker or shipped to the patient's home. The health care worker dispenses 134 the medical supplies and provides treatment to the patient in the patient's home, with any dispensed medical supplies being considered medical waste 136. The health care worker puts any medical waste into the supply package 44 which is now considered to be a medical waste container 138.

In the waste disposal and manifesting stage 140, the health care worker permanently seals the supply package 44 (now considered to be a medical waste container). A bar code on the supply package 44 acts as a manifesting identification 144 for the supply package and the sealed supply package 44 is sent to a disposal site 146, such as a medical waste disposal facility. The disposal site then confirms receipt 148 of the supply package 44, returns any necessary accounting paperwork and disposes of the supply package 44 through conventional means.

As shown in FIG. 3, the procedure followed by the supply kit assembly facility 42 comprises three stages. In the first stage 160, incoming pallets of kit packs 162 and unmade-up supply packages 164 are received by the supply kit assembly facility. In the second stage 170, incoming information on each new patient is processed by a computer 172, which then outputs data on each patient's supply package to a patient bag assembly area 174. In the patient bag assembly area, the supply packages are assembled according to the information provided in step 172. In the third stage 180, the assembled supply packages are arranged by patient name and visit number 184 and are delivered 182 to either a shipping dock or a counter for pick-up by the health care worker.

Figure 4A:
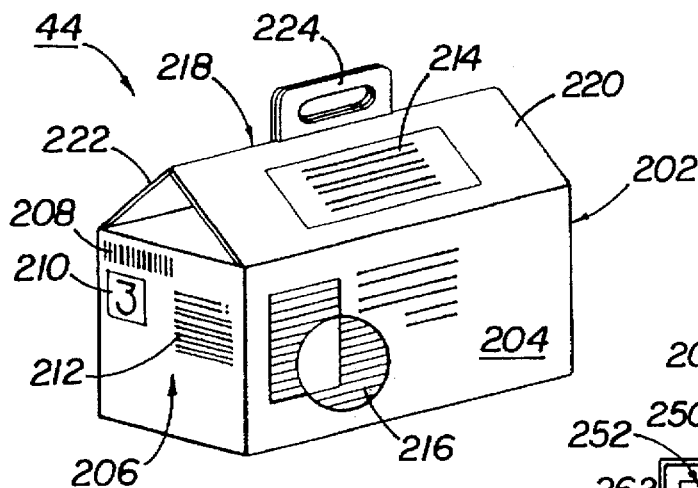
FIG. 4A is a front perspective view of a package in accordance with the present invention.
Figure 4B:
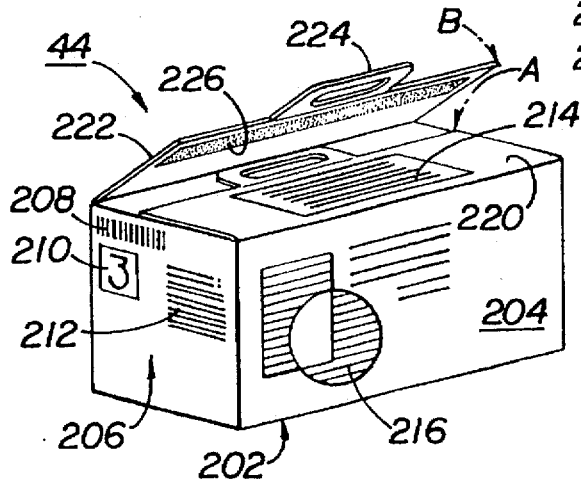
FIG. 4B is a front perspective view of a package in accordance with the present invention as it is being sealed after use.
Figure 4C:
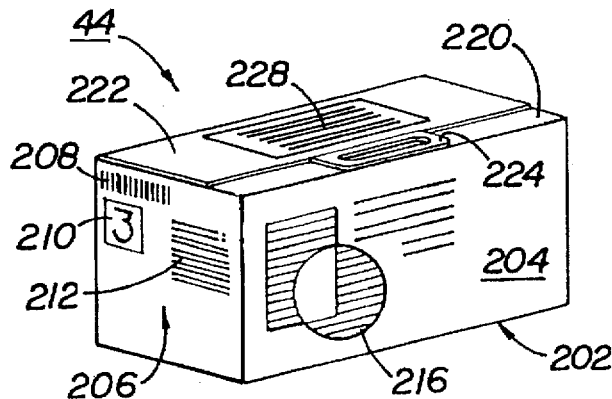
FIG. 4C is a front perspective view of a package in accordance with the present invention after it has been sealed.

As shown in FIGS. 4A–4C, the supply package 44 comprises a disposable container 202, preferably constructed from a disposable material such as cardboard, having an outside surface 204. The container 202 has a pair of top flaps 218, a first flap 220 and a second flap 222, that may comprise a handle 224 to facilitate carrying. Printed, or otherwise disposed, on the outside surface are such things as means 206 for identifying the container 202. The identifying means 206 may comprise a bar code 208, or other form of information display (such as alpha-numeric characters), used in tracking the location of the container 202, and a visit number 210 identifying where in the sequence of patient visits a given container 202 is to be used. The bar code 208 may also comprise a patient account number and a date by which the disposable container is to be delivered. Information, such as specific instructions 212 to the health care worker or delivery person, as well as a health care company service mark or other logo 216, may be printed on the outside surface 204. Rather than being printed, the identifying means 206 and other information may be applied to the container 202 in the form of a label or with any other method of applying information to containers commonly known to the art. Other information that may be applied to the outside surface 204 includes postal codes; identifiers of regulations being complied with, a shipping manifest and even a biohazard warning.

The patient's name and address 214 may be provided on the first flap 220 to facilitate delivery and to prevent errors. It may be printed on the first flap 220 or printed on a label (e.g., a removable label) placed on the first flap 220. By printing the patient's name and address 214 on the container 202, it indicates to the patient that an entire organization is involved in the patient's care. This offers the advantage of increasing the patient's confidence in the health care organization. A removable label, or a label that can be permanently covered up, may be desirable to protect the patient's privacy during the disposal process. As shown in FIG. 4B, upon completion of the patient visit by the health care worker, the first flap 220 may be folded down in direction of arrow A and the second flap 222 may be folded down on top of the first flap 220 in the direction of arrow B thereby covering the patient's address 214. A strip of two-sided tape 226, or other sealing means, may be provided to the underside of the second flap 222 so that the second flap 222 will be permanently sealed to the first flap 220 upon removing the backing of the tape 226 and folding the second flap 222 down. Any sealing means may be employed, e.g., pressure sensitive tape placed on the outside of the second flap 222, mechanical fasteners connecting the first flap 220 and the second flap 222, glue or other adhesives, or any other method of sealing containers commonly known to the art. As shown in FIG. 4C, the second flap 222 may be provided with a label 228 indicating the address of a waste disposal facility to which the container 202 is to ultimately be delivered once the container 202 is completely sealed. The label may also contain instructions for safe handling and disposal of the container 202.

Figure 5A:
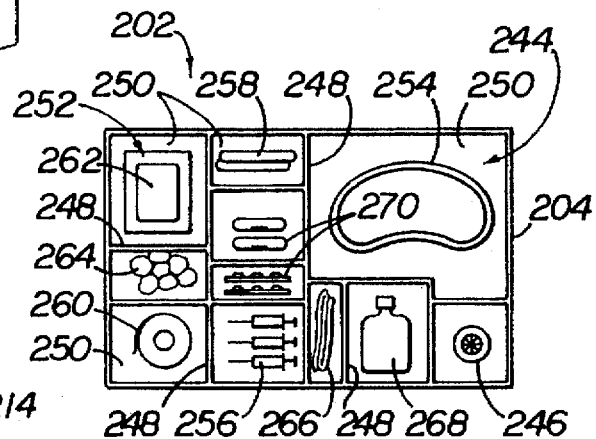
FIG. 5A is a top plan view of a partitioned package in accordance with the present invention showing a representative selection of disposable supplies disposed therein.

As shown in FIG. 5A, the container 202 (as seen from the top without showing the top flaps) comprises an outside surface 204 and an inside portion 244. Disposed within the inside portion 244 may be a disposable sharps container 246, which may or may not be affixed to the inside portion 244 (one type of suitable disposable sharps container may be of the type disclosed in U.S. Pat. Nos. 5,163,375, 5,167,193 and 5,259,501, all issued to Withers, et al., and incorporated herein by reference. As would be recognized to those skilled in the art, many other types of sharps containers may also be used.), and a plurality of upright partitions 248 defining a plurality of compartments 250 therebetween. Placed in the compartments 250 are the disposable supplies 252 required for the patient visit. Such supplies 252 may include such things as: a disposable emesis basin 254, syringes 256, tongue depressors 258, a roll of adhesive tape 260, 4×4 sponges 262, cotton balls 264, rubber tubing 266, disposable bottles of antiseptic 268, single-use medication packets 270, and any other disposable supplies used in health care. As would be obvious to one skilled in the art, the above-listed supplies are only an illustrative selection of disposable supplies and the actual configuration of supplies would depend on the specific requirements for a given patient visit.

Figure 5B:
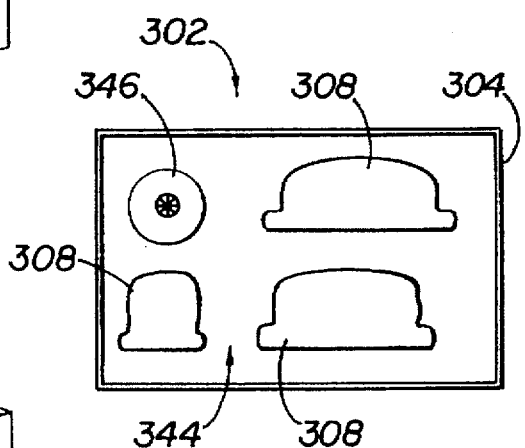
FIG. 5B is a top plan view of a non-partitioned package in accordance with the present invention showing a representative selection of disposable kit packs disposed therein.

As shown in FIG. 5B, an alternative embodiment of a non-partitioned container 302 comprises an outside surface 304 and an inside portion 344. A non-affixed sharps container 346, as well as a plurality of kit packs 308 may be disposed therein. As would be recognized by one skilled in the art, the features shown in FIGS. 5A and 5B may be readily interchanged without departing from the scope of the invention.

The above described embodiments are given as illustrative examples only. It will be readily appreciated that many deviations may be made from the specific embodiments disclosed in this specification without departing from the invention. Accordingly, the scope of the invention is to be determined by the claims below rather than being limited to the specifically described embodiments above.

I claim:

1. A method of supplying health care workers with disposable supplies appropriate for a single patient visit to a particular patient, comprising the steps of:

a. determining a requirement for disposable medical supplies for a patient for an associated single visit based on the procedures to be performed on the patient and on specific requirements for the patient;

b. placing said disposable supplies determined to be associated with the visit in a disposable container;

c. delivering said disposable container and said disposable supplies to a first site, whereat a patient is to receive treatment, prior to the associated single visit by the health care worker;

d. delivering said disposable container to a second site for disposal after the visit by the health care worker; and e. recording movement of said disposable container in a computer database when said disposable container is delivered to the first site and to the second site.

2. The method of claim 1, further comprising the step of receiving feedback information from the health care worker about the patient visit.

3. The method of claim 2, wherein said feedback information comprises information about the condition of the patient.

4. The method of claim 2, wherein said feedback information comprises information about the quantity of disposable supplies actually used during the visit.

5. The method of claim 1, further comprising the step of recording an accounting code in an accounting database, said code corresponding to said disposable supplies determined to be associated with the visit.

6. The method of claim 1, further comprising the step of posting a charge for said disposable container and said disposable supplies contained therein to an account each time one of said disposable containers is delivered to a first site.

7. The method of claim 1, further comprising the step of affixing a disposable sharps container to said disposable container.

8. The method of claim 1, wherein the first site is the patient's residence.

9. The method of claim 1, wherein the first site is a personal care facility.

10. The method of claim 1, wherein the first site is a nursing home.

11. The method of claim 1, wherein the first site is a distribution depot where the health care worker takes possession of said container.

12. The method of claim 1, wherein the second site is a medical waste disposal facility.

13. The method of claim 1, wherein the second site is a trash receptacle.

14. A method of managing supplies required by a health care worker during a single patient visit to a particular patient at a first predetermined site, comprising the steps of:

a. determining the procedures to be performed by the health worker during the single patient visit;

b. accessing a database relating the procedures to be performed on the patient to specific requirements for the patient, thereby determining a requirement for disposable supplies for the patient visit;

c. placing said disposable supplies necessary for said procedures in a disposable container; and d. delivering said disposable container to the first predetermined site prior to the single patient visit.

15. The method of claim 14, further comprising the step of delivering said disposable container to a second predetermined site subsequent to the patient visit.

16. The method of claim 15, wherein said second site comprises a medical waste disposal facility.

17. The method of claim 15, wherein said second site comprises a trash receptacle.

18. The method of claim 14, further comprising the step of transmitting to the health care worker a list of procedures to be performed during the single patient visit.

19. The method of claim 14, further comprising the step of transmitting to the health care worker directions to the patient's home.

20. The method of claim 14, wherein the first predetermined site is the patient's residence.

21. A package for use by a health care worker in performing health care services to a patient, comprising:

a. a disposable container, having an outside surface and defining an inside portion, adapted to receive disposable supplies required by the health care worker for a single visit to a single patient;

b. means, disposed on the outside of said container, for identifying said container so that it is trackable by a tracking system;

c. means, disposed on the outside of said container, for indicating an address to which said container is to be delivered; and d. means for sealing said container after use so that any material disposed therein cannot be accessed without breaking a seal, wherein said sealing means covers said address indicating means once said container has been sealed by said sealing means.

22. The package of claim 21, wherein said identifying means comprises tracking information.

23. The package of claim 22, wherein said tracking information includes a patient account number.

24. The package of claim 22, wherein said tracking information includes delivery information.

25. The package of claim 22, wherein said tracking information includes an identification of a visit number.

26. The package of claim 22, wherein said tracking information includes a date by which said disposable container is to be delivered.

27. The package of claim 21, further comprising a disposable sharps container affixed to said inside portion of said disposable container.

28. The package of claim 21, further comprising a disposable sharps container placed within said disposable container.

29. The package of claim 21, wherein said identifying means comprises a bar code printed on the outside of said disposable container.

30. The package of claim 21, wherein said identifying means comprises a label applied to the outside of said disposable container.

31. The package of claim 21, wherein said identifying means comprises alpha-numeric characters applied to the outside of said disposable container.

32. A package for use by a health care worker in performing health care services to a patient, comprising:

a. a disposable container, having an outside surface and defining an inside portion, adapted to receive disposable supplies required by the health care worker for a single visit to a single patient;

b. means, disposed on the outside of said container, for identifying said container so that it is trackable by a tracking system;

c. means, disposed on the outside of said container, for indicating an address to which said container is to be delivered;

d. means for sealing said container after use so that any material disposed therein cannot be accessed without breaking a seal; and e. means for indicating an address of a waste disposal facility, wherein said address indicating means is a removable label.

33. A package for use by a health care worker in performing health care services to a patient, comprising:

a. a disposable container, having an outside surface and defining an inside portion, adapted to receive disposable supplies required by the health care worker for a single visit to a single patient:

b. means, disposed on the outside of said container, for identifying said container so that it is trackable by a tracking system;

c. means, disposed on the outside of said container, for indicating an address to which said container is to be delivered;

d. means for sealing said container after use so that any material disposed therein cannot be accessed without breaking a seal; and e. means for indicating an address of a waste disposal facility wherein said indicating means is visible on the outside of said container only after said container has been sealed with said sealing means.

* * * * *